United States Patent [19]

Vukovich

[11] Patent Number: 5,112,949

[45] Date of Patent: May 12, 1992

[54] METHOD OF AND APPARATUS FOR SEPARATING PROTEINS

[76] Inventor: Thomas Vukovich, 1080 Vienna Langegasse 70, Austria

[21] Appl. No.: 26,868

[22] Filed: Mar. 17, 1987

[30] Foreign Application Priority Data

Mar. 27, 1986 [AT]  Austria ............................ A827/86

[51] Int. Cl.$^5$ .................. A61K 35/14; C07K 3/02; C07K 3/20; C07K 3/28
[52] U.S. Cl. ............................... 530/380; 530/381; 530/382; 530/413; 530/416; 530/417; 530/830; 530/831
[58] Field of Search ............... 530/380, 381, 382, 413, 530/416, 417, 830, 831; 424/101

[56] References Cited

U.S. PATENT DOCUMENTS

| | | |
|---|---|---|
| 4,447,416 | 5/1984 | Menache Aronson et al. ..... 424/101 |
| 4,696,895 | 9/1987 | Yamashita et al. ................. 530/387 |
| 4,770,781 | 9/1988 | Schmildt et al. ................... 530/417 |

FOREIGN PATENT DOCUMENTS 0208215  1/1987  European Pat. Off.

OTHER PUBLICATIONS

Miyashita et al., in "Protein C, Biochemical and Medical Aspects", Witt (Ed.), Wde G. Berlin/N.Y., (1985), pp. 59–65.
Comp et al., Blood. 63 15-21 (1984).
Sugo et al., J. Biol. Chem. 260 (19), 10453, (1985).
Kisiel et al., J. Clin. Invest., 761-769, (1979), vol. 64.
Pahlback et al., Biochem. J., 209, 837-846 (1983).
Suzuki et al., J. Biol. Chem. 258, 1914-1920, (1983).
Stenflo et al., FEBS Lett, 101(2), 377-381, (1979).

*Primary Examiner*—Jeffrey E. Russel
*Attorney, Agent, or Firm*—Henry M. Feiereisen

[57] ABSTRACT

A method of and apparatus for separating proteins adsorbed by ion-exchange gels, especially anion-exchanging gels includes at least one chromatographic column in which the protein-carrying gel is charged and is subjected to a gradient-elution with a buffer solution as eluant whose property is changed with time by gradually changing the ionic strength and maintaining a substantially constant pH value or by gradually changing the pH value and maintaining substantially a constant ionic strength. The obtained eluate is then fractionated into its various components.

21 Claims, 2 Drawing Sheets

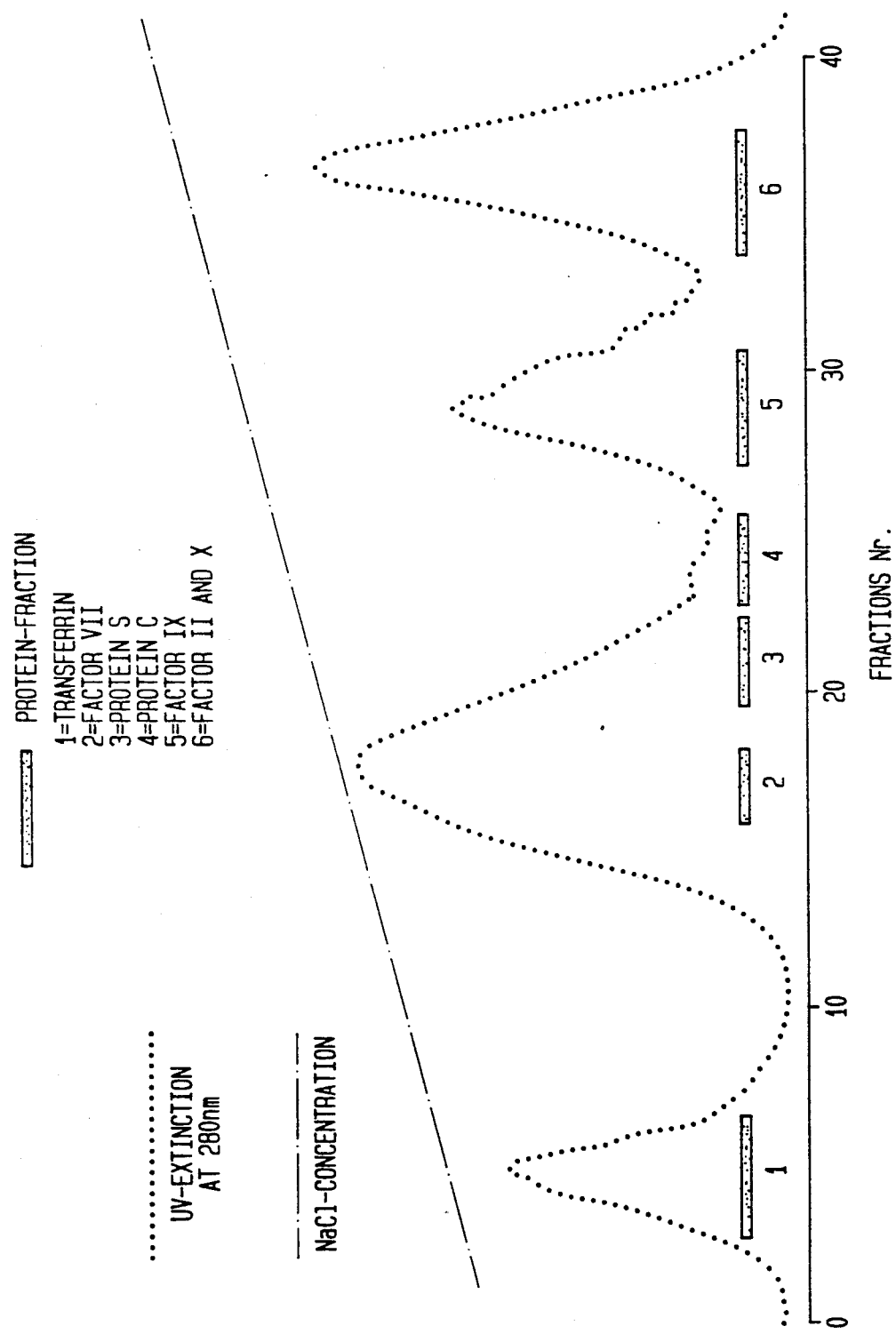

METHOD OF AND APPARATUS FOR SEPARATING PROTEINS

BACKGROUND OF THE INVENTION

The present invention relates to a method of and apparatus for separating proteins, in particular proteins from human plasma, from residues of human plasma cryoproteins or residues of cell cultures which proteins are adsorbed by ion-exchange gels, especially anion-exchanging gels like diethylaminoethyl (DEAE) gels. In addition, the present invention refers to pharmaceutical compositions containing such fractions of proteins.

The adsorption of a number of plasma proteins by gels carrying charged groups at their surface and added to blood plasma is known. The surface retention of proteins by these gels is dependent on the functional group of the respectively used gel i.e. whether the functional group is positive or negative and thus adsorbs anions or cations and on the dissociation constant of the charged group, and is further dependent on the prevailing conditions during mixing of the gel with the blood plasma, primarily on the ionic concentration, the kind of dissolved ions, the pH, and the temperature.

When adding to the blood plasma gels having as functional group an anion-exchanging effect as e.g. DEAE-gels, plasma proteins are adsorbed by the gel which are known as "factors of the prothrombin complex". The protein-loaded gel can then simply be separated from the residual plasma. Since the bonding strength between the plasma proteins and the ion-exchanging gels decreases with increasing ionic concentration of the surrounding solution, the proteins can be desorbed from the gel in solutions of high ionic strength. The German patent DE-PS 2 715 832, East German patents DD 148,297 and DD 141,261 and European patent EP 0041173 disclose methods by which the factors of the prothrombin complex are adsorbed from the blood plasma by DEAE-gels and together desorbed without separation into individual components of the prothrombin complex through washing of the gels with solutions of high ionic strength.

It is also known that the prothrombin complex contains various proteins as e.g. the blood clotting factors F II, F VII, FIX F X, as well as blood clotting inhibitors like protein C and protein S. Each component of the prothrombin complex has different biological effects, especially when considering the blood clotting factors and the blood clotting inhibitors which are completely antagonistic to each other.

The medical literature describes genetical diseases which manifest themselves by the incapability of a patient to synthesize one component of the prothrombin complex so that the blood plasma of such a patient lacks this component. A deficiency of one of the clotting factors leads to hemophilia e.g. a deficiency of factor IX results in hemophilia B, while a deficiency of one of both blood clotting inhibitors leads to thrombosis in the patient. The therapy of these completely different diseases comprises, however, the use of an identical plasma derivative that is prothrombin complex to compensate for the deficiency. Evidently, the simultaneous administration of the deficient clotting factor with blood clotting inhibitors may increase the tendency for bleeding in hemophiliacs while in patients suffering of thrombosis, the simultaneous administration of clotting factors in addition to the required inhibitors may further increase the risk of thrombosis.

It is certainly preferable to treat a patient with a deficiency of one clotting factor with a preparation containing only the deficient clotting factor and otherwise being free of inhibitors, and to treat a patient who is deficient of one of the inhibitors with a preparation containing only the concerned inhibitor without any clotting factors.

A method for essentially separating the components of the prothrombin complex is e.g. disclosed by S. P. Bajaj et al. in the publication Preparative Biochemistry, 13 (3), 191–214, 1983. The method comprises a sequence of steps: After saturation of the plasma with ammonium sulphate to 33%, the precipitated proteins are hurled off and the supernatant residue is enriched with ammonium sulphate to 66% or 70% saturation. The precipitated proteins are hurled off and redissolved in saline solution. Barium salt (BaCl or $BaSO_4$) is added and the precipitated proteins are hurled off and redissolved in saline solution. The precipitation with barium salt may also be carried out prior to the differential precipitation with ammonium sulphate. Subsequently, the proteins are subjected to adsorption on a DEAE-gel column and fractional desorption by gradient elution with a gradient of increasing ionic strength in the elution buffer. After this gel chromatography, the components of the prothrombin complex are, however, not yet entirely separated so that a further step is proposed which comprises a preparative acrylamide electrophoresis.

The above described fractionation method is only suitable to prepare the factors of the prothrombin complex on a laboratory scale for biochemical in vitro tests or for immunization of animals for the production of antisera. According to the prior art, the acrylamide electrophoresis works only with low amounts of protein like less than 5,000 plasma units of e.g. factor IX. Moreover, apart from the electrophoresis, the remaining steps of this method are very time consuming and require the use of protease inhibitors like benzamidine in order to reduce the enzymatic denaturation of the proteins during this lengthy method. As is well documented, these protease inhibitors are of considerable toxicity so that their application in protein preparations for humans is not possible. Further, the use of barium salt for precipitation is undesirable as these compounds are toxic as well.

SUMMARY OF THE INVENTION

It is thus an object of the present invention to provide an improved method of separating components of proteins in particular prothrombin complex adsorbed by ion-exchange gels, obviating the afore-stated drawbacks.

This object and others which will become apparent hereinafter, are attained by gradient-eluting the proteins adsorbed by the gel in a chromatographic column with a buffer solution of gradually changing ionic strength and substantially constant pH value or gradually changing pH value and substantially constant ionic strength so as to gradually desorb the proteins from the gel and to provide an eluate, and by fractionating the eluate into separate protein fractions.

According to a further feature of the invention, the gradient-elution is obtained by continuously changing the ionic strength of the buffer solution between 100 and 400 mval and 400 and 4000 mval while its pH value is maintained at a substantially constant level ranging from 5 to 8. Alternatingly, the pH value may be continuously changed in a range between 3 and 9 while the ionic strength is substantially kept at constant level in a range from 100 to 400 mval, preferably between 100 and 400 mval.

It has been found especially advantageous to operate with anion-exchanging gels, and in particular with DEAE-gels, and to use the buffer solution as eluant with increasing ionic strength and substantially constant pH value or with increasing pH value and substantially constant ionic strength to attain the desired gradient-elution.

According to a further feature of the present invention, one embodiment of an apparatus for separating proteins adsorbed by ion-exchanging gels includes a chromatographic column, a first reservoir connected to the chromatographic column and containing a first buffer solution, a second reservoir connected to the chromatographic column and being divided into two compartments linked to each other. One of the compartments contains the first buffer while the other compartment contains a second buffer of greater elution power so as to define a gradient when gradually mixing the second buffer with the first buffer.

Preferably, an agitator is located within one of the compartments of the second reservoir to provide a thorough mixing when introducing the second buffer into the first buffer. The eluate discharged from the chromatographic column is monitored by a suitable control unit in dependence on the UV-extinction of the eluate.

With the present invention, the components of proteins, as e.g. the factors of the prothrombin complex and transferrin, can be purified on a large scale without requiring the use of toxic protease inhibitors or toxic barium salts. Thus, the individual components of the proteins are free of toxic constituents and superior to the produced components obtained by the small scale method as disclosed by S. P. Bajaj. The products obtained during the method according to the invention are suitable to be administered in humans and correspond to the European pharmacopoeia.

DESCRIPTION OF PREFERRED EMBODIMENTS

The following example is set forth to illustrate the method of separating a prothrombin complex into its components in accordance with the invention. This example is set forth by way of example only and not intended in a limiting sense.

1. Adsorption of Plasma Proteins by Ion-Exchange Gels.

An ion-exchange gel e.g. DEAE gel in dry condition or swelled in aqueous solution is added to blood plasma or a blood plasma fraction like blood plasma after removal of cryoproteins. The gel is agitated with the protein solution until the desired protein components are essentially adsorbed by the gel. Transferring and factors of the prothrombin complex (F II, F VII, F IX, F X, protein C, protein S) are all adsorbed by the DEAE gel in this manner.

Specifically, DEAE gel, preferably DEAE-Sephadex A50, is added at a temperature between 0°-20° C., preferably 0° C., to the blood plasma which is freed of cryoproteins, at an amount of 0.2-10 gram per liter plasma, preferably 0.5 gram per liter plasma. The gel is maintained in suspension within the plasma solution by agitating for ¼-10 hours, preferably 4 hours.

Thereafter, the gel is separated from the remaining residual plasma by sedimentation through gravitational force or by centrifugation and subsequent separation of the supernatant residual plasma.

2. Gel Chromatographic Separation of the Proteins Adsorbed by the Gel

BRIEF DESCRIPTION OF THE DRAWINGS

For describing this method step in more detail, reference is made to the accompanying drawing of an apparatus according to the invention in which:

FIG. 2 is a graphical illustration of an chromatogram.

Referring now to FIG. 1, there is shown a schematic illustration of one embodiment of an apparatus for separating proteins into its components in accordance with the invention and including a first chromatographic column GS1 which is connected via a pump P1 and three-way valve V1 to a first reservoir R1 containing a buffer solution PR1 which has a salt concentration and pH value suitable to allow the proteins to be fractionated to remain adsorbed by the gel, however, undesired proteins with lower affinity to the gel to be washed away.

Figure 1:
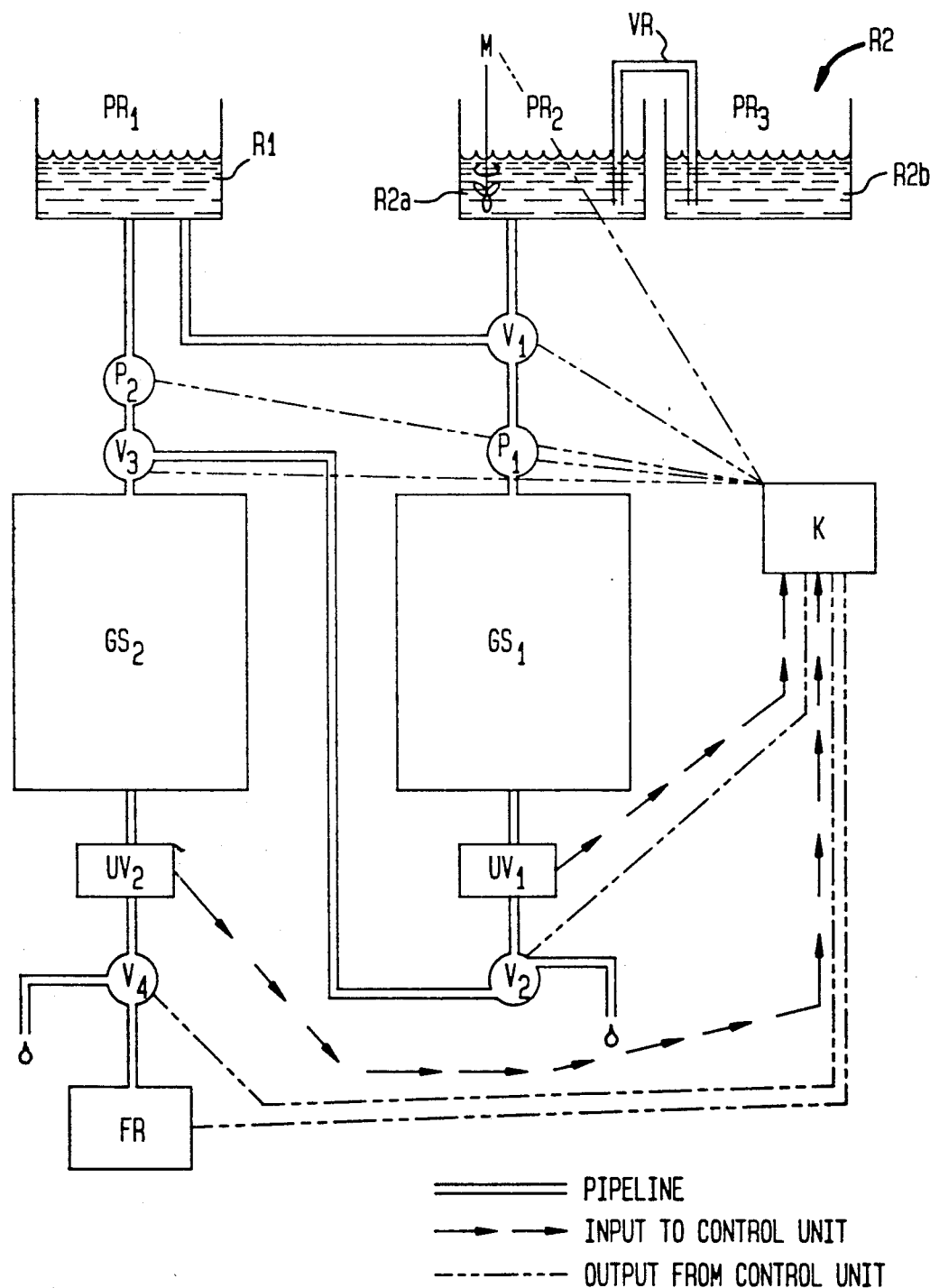
FIG. 1 is a schematic illustration of one embodiment of an apparatus for separating the components of a protein complex in accordance with the invention.

Successively connected to the chromatographic column GS1 via suitable three-way valves V2 and V3 is a second chromatographic column GS2 which is linked to the reservoir R1 via a pump P2. A three-way valve V4 connects the column GS2 with a fraction collector FR. The column GS1 is further connected via the valve V1 to a second reservoir R2 with two compartments R2a and R2b communicating with each other via a pipeline VR provided with a vent (not shown). The compartment R2a contains a buffer solution PR2 which is the same buffer solution PR1 as in the reservoir R1 and accommodates an agitator M for mixing the solution contained therein. The compartment R2b contains a buffer solution PR3 of greater elution power than buffer solution PR2 with a salt concentration and H+-ionic concentration sufficient to desorb all desired plasma proteins from the gel.

By connecting the compartments R2a and R2b via pipeline VR, a gradient is defined by either gradually increasing the ionic strength of the buffer solution PR2 through introduction of buffer solution PR3 and substantially maintaining the pH value at a constant level or by gradually increasing the pH value and maintaining the ionic strength at a substantially constant level. In the first case, the ionic strength of the buffer solution supplied to the column GS1 is gradually changed in the range of 100 to 4000 mval, preferably 100 and 400 mval while the pH value is essentially kept constant within the range of 5 to 8. In the latter case, the pH value is continuously changed in the range of 3 to 9 while the ionic strength is kept constant at a level in the range between 100–400 mval and 400–4000 mval.

Associated to each column GS1, GS2 at their outlet is an ultraviolet (UV) measuring instrument UV1, UV2. As indicated by the arrows, the UV-measuring instruments UV1, UV2 send a signal to a control device K in dependence on e.g. the UV-absorption of the protein concentration in the eluate of the columns GS1, GS2 to indicate the end of the equilibration and washing step in columns GS1, GS2 and the fractionation of the eluate. Depending on the information given by the UV-measuring instruments UV1, UV2, the control device K actuates the valves V1, V2, V3, V4, pumps P1, P2 and agitator M as indicated by the broken line.

The apparatus in accordance with the invention allows in a preferred embodiment a computer-controlled fractionation of proteins adsorbed by the gel and operates as follows:

The protein-loaded gel is supplied into the column GS1 and protein-free gel is filled into columns GS2. Both columns GS1, GS2 are then closed. Via the valves V1 and V3, the columns GS1, GS2 are eluted with buffer solution PR1 from reservoir R1. In column GS1, undesired proteins are washed out from the gel while column GS2 is equilibrated by the buffer solution PR1. In order to achieve a satisfactory washing and equilibration of the respective columns GS1, GS2, a buffer volume is calculated which is three times the volume of the columns.

As soon as all the proteins which at the prevailing conditions of the buffer PR1 do not have any affinity to the gel are washed out, the UV-extinction of the eluate drops and the UV-measuring instrument UV1 transmits a corresponding signal to the control device K which thus terminates the washing step. At the same time the control device K actuates the valves V1, V2, V3 in such a manner that the column GS1 is supplied with buffer solution PR2 from compartment R2a of reservoir R2 and the resulting discharge of column GS1 is fed to column GS2 which is disconnected from reservoir PR1 by valve V3. Simultaneously with the open connection of the column GS1 with the compartment R2a of reservoir R2, the agitator M is actuated and buffer solution PR3 is pumped from compartment R2b to compartment R2a through pipeline VR by a suitable pump (not shown) while pump P2 is switched off. Consequently, a gradient is defined by the linked compartments R2a, R2b of the reservoir R2 so that the various proteins adhering to the gel within column GS1 are eluted depending on their affinity to the gel. In column GS2, the proteins are again adsorbed for a short period by the gel whose functional groups are essentially vacant. A desorption occurs with further ascent of the gradient resulting in a considerable increase of the sharpness of separation of the chromatography.

As soon as the UV-extinction increases in the eluate of the column GS2, the eluate is discharged to the fraction collector FR via valve V4. The fraction collector FR can accumulate the fractions according to constant volume or may be peak-controlled (according to extinction peaks) in order to form fractions.

It should be noted that the use of two such columns is not required; rather the method according to the invention can be carried out by an apparatus which includes only one such column, like column GS1. Moreover, the described method may be modified by forming a lower layer of uncharged equilibrated gel under the protein-charged gel in the chromatographic column.

In the following, the method and the apparatus according to the invention are described by way of an example with respect to fractionation of transferrin and factors of the prothrombin complex by chromatography with DEAE-gel. This example is set forth by way of illustration only and not intended in a limiting sense.

Column GS1 of a diameter of e.g. 10 cm and a length of e.g. 40 cm is filled with protein-loaded DEAE gel (31 wet gel), and column GS2 of a diameter of e.g. 10 cm and c length of e.g. 40 cm is filled with DEAE gel, preferably DEAE-Sephadex A50), at a same gel volume as in column GS1. This gel is swelled in buffer PR1 which consists preferably of 0.02 mol phosphate, 0.01 mol citrate, 0.15 mol NaCl in $H_2O$ and has a pH 6 adjusted with NaOH at 20° C. The columns GS1, GS2 are separately washed with buffer PR1, preferably 3 liter buffer per liter column volume at a buffer flow rate of about 21 per hour. After having sequentially connected the columns GS1, GS2, the gradient elution (buffer flow rate about 21 per hour) is started by introducing buffer PR3 from compartment R2b into compartment R2a. The volume of buffer PR3 in compartment R2b corresponds preferably to the volume of buffer PR2 in compartment R2a. Buffer solution PR3 consists preferably of 0.02 mol phosphate, 0.01 mol citrate, 0.5 mol NaCl in $H_2O$ and has a pH 6 adjusted with NaOH at 20° C.

As soon as the UV-measuring instrument UV2 located at the outlet of column GS2 registers an increase of the UV-extinction, the fractions are collected. Preferably, an eluate volume of ½ liter per fraction is collected in case the overall volume in the compartments R2a, R2b of reservoir R2 is 20 liter=40 fractions. A reference sample is drawn from each fraction for analysis. These reference samples are examined as to their protein content, content of factors II, VII, IX, X as well as to their content of protein C and protein S according to methods described further below.

Turning now to FIG. 2 which illustrates a typical elution diagram of transferrin as well as the components of the prothrombin complex. In case a protein component was eluted in several adjoining fractions, these fractions were combined and processed for application in humans according to known methods like dialysis, heat treatment, for viral deactivation, bulk lyophylization, dissolving in water and adjusting of the salt content and pH value, sterilization by filtration and bottling in containers, lyophilization of the end product.

The sequence of the elution can be modified at different conditions of the initial product and method parameters. The method is in particular favorable for isolating protein C and protein S.

In the following, the methods for determining transferrin, factor II, VII, IX and X, protein S and protein C are indicated.

A) Transferrin

Determination through electroimmunodiffusion method according to Laurell by using an antiserum specific for human transferrin.

B) Factor II

Determination through electroimmunodiffusion method according to Laurell by using an antiserum specific for human factor II. Functional determination with the thromboplastin time (time for conversion of prothrombin to thrombin) by using a plasma deficient of factor II.

C) Factor VII

Functional determination with the thromboplastin time by using a plasma deficient of factor VII.

D) Factor IX

Determination through electroimmunodiffusion method according to Laurell by using an antiseru specific for human factor IX. Functional determination with the activated partial thromboplastin time by using a plasma deficient of factor IX.

E) Factor X

Functional determination by means of the thromboplastin time by using a plasma deficient of factor X.

F) Protein C

Determination through enzyme immunological detection with a test kit commercially available under the name "ELISA Protein C".

Functional determination according to the method disclosed in Wiener Klinische Wochenschrift 97, 9, 1985, 445 by Th. Vukovich, or with a test kit commercially available through Behring Diagnostika. The latter method proved extremely favorable for quality control of the product.

An exemplified test method for clotting promoting components in order to identify the fraction protein C is as follows:

A sample of the eluate is incubated with insoluble thrombin which is subsequently removed by centrifugation while the supernatant residue is mixed in a ratio 1+1 with standard plasma. The activated partial thromboplastin time of the mixture is determined by comparison with a control preparation of standard plasma and buffer. Presence of protein C in the sample is indicated by the prolongation of the activated partial thromboplastin time in comparison to the control preparation while a shortening of the thromboplastin time indicates the presence of clotting factors in the sample.

G) Protein S

Functional determination through determination of the exponentiation of the inhibiting effect of thrombin-sepharose activated protein C to the activated partial thromboplastin time of a protein S deficiency and plastic.

Indication of the Protein Fractions Separated by the Method According to the Invention

1. Fraction Transferrin

Application in innate or acquired deficiency of transferrin; in iron-deficient anemia, in bacterial infections; in malignant neoplasms.

2. Fraction Factor II

Application in innate or acquired deficiency of factor II, application together with fibrinogen as "fibrin adhesive" in wound treatment.

3. Fraction Factor VII

Application in innate or acquired deficiency of factor VII, application in hemophilia A and hemophilia B.

4. Fraction Factor IX

Application in innate or acquired deficiency of factor IX, application in hemophilia A and hemophilia B.

5. Fraction Factor X

Application in innate or acquired deficiency of factor X, application in hemophilia A and hemophilia B.

6. Fraction Protein C

Application in innate or acquired deficiency of protein C, in peripheral and central vascular diseases, venous diseases; thromboembolism; disseminated intravascular coagulopaty (DIC); for thrombosis prophylaxis; for prophylaxis and therapy of Markoumar-induced skin necrosis; in respiratory distress syndrome; protein S deficiency; chemotherapy.

7. Fraction Protein S

Application in innate or acquired deficiency of protein S; deficiency of protein C; all applications listed under 6.

8. Combined Fraction of Protein C and Protein S

Application as listed under 6 and 7.

Characteristic Composition of Protein Fractions Separated in Accordance with the Method of the Invention (Purity Criteria)

1. Fraction Transferrin

More than 90% of the protein contained in the fraction is transferrin; no isoagglutinins Anti-A, Anti-B traceable. Less than 10 plasma units of factor II, VII, IX, X, protein C and protein S per gram transferrin

2. Fraction Factor VII

No isoagglutinins Anti-A, Anti-B traceable. Less than 0.2 plasma units of factor II, IX, X, protein C and protein S per plasma unit of factor VII.

3. Fraction Protein S

In a concentration of 50 plasma units of protein S per ml solution: no agglutination with erythrocytes of blood group A or B is visibly detectable; contains less than 10 plasma units of factor VII, II, IX, X; no activating clotting factors traceable with non-activated partial thromboplastin time; no shortening of the activated partial thromboplastin time detectable after incubation with thrombin-sepharose (40 NIH-units per ml for 2 hours at 37° C.) and removal of thrombinsepharose in a mixture with standard plasma (1+1 parts); contains less than 10 mg protein.

4. Fraction Protein C

In a concentration of 50 plasma units of protein C per ml solution: no agglutination with erythrocytes of blood group A or B is visibly detectable; less than 10 plasma units of factor VII, II, IX, X is traceable; a prolongation rather than a shortening of the activated partial thromboplastin time is determinable after incubation with thrombin-sepharose (40 NIH-units per ml mixture for 2 hours at 37° C.) and removal of thrombinsepharose in a mixture with standard plasma (1+1 parts); no activated clotting factors detectable with non-activated partial thromboplastin time; contains less than 10 mg protein.

4a. Fraction Protein C and Protein S

In a concentration of 30-50 plasma units of protein C and protein S per ml solution: no agglutination with erythrocytes and blood group A or B is visibly detectable; less than 10 plasma units of factors VII, II, IX, X is traceable; a prolongation rather than a shortening of the activated partial thromboplastin time is determinable after incubation with thrombin-sepharose (40 NIH-units per ml mixture for 2 hours at 37° C.) and removal thromboplastin time; contains less than 10 mg protein. (1+1); no activated clotting factors detectable with non-activated partial thromoplastin time; contains less than 10 mg protein.

5. Fraction Factor IX

In a concentration of 50 plasma units of factor IX per ml solution: no agglutination with erythrocytes of the blood group A or B is visibly detectable; contains less than 10 plasma units of protein C and protein S; no activated factors detectable with non-activated partial thromboplastin time (without addition of heparin and/or antithrombin III); contains less than 20 mg protein.

6. Fraction Factor II

In a concentration of 50 plasma units of factor II per ml solution: no agglutination with erythrocytes of the blood group A or B is visibly detectable; contains less than 10 plasma units of protein C and protein S.

7. Fraction Factor X

In a concentration of 50 plasma units of factor X per ml solution: no agglutination with erythrocytes of the blood group A or B; contains less than 10 plasma units of protein C and protein S; no activated clotting factors traceable with non-activated partial thromboplastin time (without addition of heparin and/or antithrombin III); contains less than 20 mg protein.

It will thus be seen that the objects set forth above, among those made apparent from the preceding description, are efficiently attained and, since certain changes may be made in carrying out the above process and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

I claim:

1. A method of separating proteins from human plasma, from residues of human plasma cryoproteins or from residues of cell cultures, with the proteins having been adsorbed on an anion-exchanging gel; comprising in succession the steps of:
    gradient-eluting the proteins adsorbed on the gel in a chromatographic column with a buffer solution as eluant defined by two parameters one of which being gradually changed while the other one is maintained at a substantially constant level so as to gradually desorb the proteins from the gel, said parameters being ionic strength and pH value;
    purifying the desorbed proteins by adsorbing the proteins immediately after being desorbed from the anion-exchanging gel on protein-free and equilibrated gel and subsequently desorbing the proteins by changing the buffer solution through further increase of the one parameter so as to obtain an eluate at increased sharpness of separation of the proteins; and
    fractionating the eluate into separate protein fractions.

2. A method as defined in claim 1 wherein said separating step includes fractionating the eluate in fractions selected from the group consisting of transferrin, factor II, factor VII, factor IX, factor X, protein C and protein S.

3. A method as defined in claim 1 wherein said gradient-eluting step includes gradually changing the ionic strength of the buffer solution and maintaining the pH value of the buffer solution at a substantially constant level.

4. A method as defined in claim 3 wherein the ionic strength of the buffer solution is continuously changed in a range between 100-400 mval and 400-4000 mval, and the pH value is maintained at a substantially constant level in a range of 5 to 8.

5. A method as defined in claim 1 wherein said gradient-eluting step includes gradually changing the pH value and maintaining the ionic strength at a substantially constant level.

6. A method as defined in claim 5 wherein the pH value of the buffer solution is continuously changed in a range between 3 and 9, and the ionic strength is maintained at a substantially constant level in a range of 100 to 400 mval.

7. A method as defined in claim 6 wherein the ionic strength is maintained substantially at a constant level in the range of 100 to 400 mval.

8. A method as defined in claim 1 wherein the anion-exchanging gel is diethylaminoethyl (DEAE) gel.

9. A method as defined in claim 8 and further comprising the step of equilibrating the anion-exchanging gel loaded with the adsorbed proteins with a further buffer solution of lowest ionic strength prior to said gradient-eluting step.

10. A method as defined in claim 8 and further comprising the step of equilibrating the anion-exchanging gel loaded with the adsorbed proteins with a further buffer solution of highest pH value prior to said gradient-eluting step.

11. A method as defined in claim 1 wherein said gradient-eluting step includes adjusting the elution gradient in the eluant by adding a first buffer of an ionic strength of 100 to 400 mval to a second buffer of an ionic strength of 400 to 4000 mval.

12. A method as defined in claim 1 wherein said gradient-eluting step includes adjusting the elution gradient in the eluant by adding a first buffer of a pH value of 6 to 8 to a second buffer of a pH value of 5 to 7.

13. A method as defined in claim 1, and further comprising the step of monitoring the UV-extinction of the eluate.

14. A method as defined in claim 1, and further comprising the step of identifying the fractions through immunological processes by using antisera specific for the proteins to be identified.

15. A method as defined in claim 1, and further comprising the step of identifying the fractions through functional processes characteristic for the proteins to be identified.

16. A method as defined in claim 2, and further comprising the step of identifying the presence of protein C and clotting factors by incubating a sample of the eluate with insoluble thrombin, removing the thrombin through centrifugation from the supernatant residue, mixing the residue in a ratio of 1+1 with standard plasma and comparing the activated partial thromboplastin time of the mixture with the one of a control preparation wherein a prolongation of the activated partial thromboplastin time of the mixture indicates the presence of protein C while a shortening thereof indicates the presence of clotting factors.

17. A method as defined in claim 16 wherein the control preparation includes standard plasma and buffer solution.

18. A method as defined in claim 11 wherein the first and second buffers are each selected from the group consisting of phosphate, citrate, NaCl and NaOH.

19. A method as defined in claim 1, and further comprising the step of introducing a buffer solution of suitable ionic strength and pH value into the chromatographic column for washing out undesired proteins prior to said gradient-elution step.

20. A method as defined in claim 19 wherein the buffer solution is introduced at a volume which is three times the volume of the chromatographic column.

21. A method as defined in claim 1 wherein said purifying step includes directly transferring the desorbed proteins from the chromatographic column to a further chromatographic column which contains the protein-free and equilibrated gel to allow adsorption of the proteins thereon and further increasing the gradient as defined by the buffer solution for eluting the proteins in the second chromatographic column.

* * * * *